(12) United States Patent
Steddin

(10) Patent No.: US 6,506,050 B1
(45) Date of Patent: Jan. 14, 2003

(54) DENTAL DEVICE AND METHOD FOR CONTROLLING SAME

(75) Inventor: Sven-Dieter Steddin, Biberach (DE)

(73) Assignee: Kaltenbach & Voigt GmbH, Biberach (DE)

(*) Notice: Subject to any disclaimer, the term of this patent is extended or adjusted under 35 U.S.C. 154(b) by 12 days.

(21) Appl. No.: 09/664,786

(22) Filed: Sep. 19, 2000

(30) Foreign Application Priority Data

Oct. 8, 1999 (DE) .......................................... 199 48 620

(51) Int. Cl.[7] .................................................. A61C 3/00
(52) U.S. Cl. .......................................... 433/98; 433/27
(58) Field of Search ................................ 433/98, 28, 27

(56) References Cited

U.S. PATENT DOCUMENTS

| 5,230,623 A | 7/1993 | Guthrie et al. ............... 433/72 |
| 5,300,926 A | 4/1994 | Stoeckl ....................... 345/157 |
| 5,359,511 A | * 10/1994 | Schroeder et al. ..... 364/413.28 |
| 5,688,118 A | * 11/1997 | Hayka et al. ............ 433/27 X |
| 5,828,197 A | 10/1998 | Martin et al. ............... 318/567 |
| 5,902,105 A | * 5/1999 | Uejima et al. ............ 433/27 X |

FOREIGN PATENT DOCUMENTS

| DE | 29621939 U1 | 5/1998 |
| EP | 0391967 B1 | 8/1992 |
| EP | 0525539 A2 | 2/1993 |
| EP | 0526015 A1 | 2/1993 |
| EP | 0455852 B1 | 8/1994 |
| EP | 0789320 A2 | 8/1997 |

* cited by examiner

Primary Examiner—Nicholas D. Lucchesi
Assistant Examiner—Melba Bumgarner
(74) Attorney, Agent, or Firm—Fitzpatrick, Cella, Harper & Scinto

(57) ABSTRACT

In order to control a dental device having at least one treatment instrument (1), a central control device and a display unit (2), the device has additional means (4, 5, 6) for detecting the spatial position of the treatment instrument (1). In a control mode, the detected spatial position of the treatment instrument (1) is converted by the control device into coordinates for controlling and operating a pointer (3) on the display unit (2). The treatment instrument (1) is thus also used as an input instrument, its method of functioning being similar to that of a computer mouse.

11 Claims, 2 Drawing Sheets

DENTAL DEVICE AND METHOD FOR CONTROLLING SAME

BACKGROUND OF THE INVENTION

1. Field of the Invention

The present invention relates to a dental device and also to a method for effectively controlling this device.

2. Description of the Related Art

In modern medical devices, a plurality of functions of the medical equipment often have to be controlled with the aid of different control devices. For example, in the course of a complex treatment with a plurality of consecutive treatment steps, the operating parameters of the different pieces of equipment are chosen specially for each treatment step. In this connection, both the treatment instruments themselves and also, for example, the patient chair or further auxiliary devices are to be classed as pieces of equipment.

Several publications deal with a simple and effective control of the different functions of medical devices. In this connection, particularly in the case of dental devices, the foot switch is still the most frequently used input device. Further developments of the classic foot switch are, for example, known from EP 0 525 539 A2. In this connection, by way of pressure sensors, the loads on the surface of the foot switch are converted into primary electrical signals, which are converted into control signals by means of signal evaluating electronics and transmitted to a central control unit. In this way, a dental treatment device having a patient chair and a plurality of dental apparatuses is controlled. A dental device described in EP 0 455 852 B1 furthermore has a display device on which all of the important functions of the device are represented. The operating of the different functions is enabled only by a single input instrument, namely a foot switch which is adjustable in two degrees of freedom. The dental device disclosed in EP 0 391 967 B1 also enables a control of all of the operations and auxiliary functions by way of only a single foot switch.

Because dental treatment areas are being constructed in ever more complex and diverse ways, the control of all of the functions of a treatment area by a single foot switch is more and more difficult to manage. The possibilities of a foot switch as control device are namely restricted because of the operation with the feet and the degree of freedom available. In order to alter a single parameter, it is often necessary to select a series of sub-menus, until finally the desired alteration can be carried out. But the numerous input steps required in order to do this and the time expenditure linked therewith cannot necessarily be seen as very user-friendly.

The medical device described in DE 296 21 939 U1 therefore has an input device which contains a pointer device, preferably a mouse pad with pressure and position sensor technology, by way of which the different functions of the device, the corresponding parameters of which are represented on a display unit, can be controlled by hand. A foot switch is used as a further input apparatus, by way of which foot switch the control of the treatment instrument being used at the time takes place.

Finally, the position-detection of medical treatment instruments is known from neurosurgery. In operations carried out in this field, it is often essential to know the exact position of the treatment instrument relative to the anatomy of the patient in order to be able to carry out the operation with very high precision at the place to be treated. Neurosurgical treatment devices therefore basically have a treatment instrument and also a display unit and means for detecting the position of the treatment instrument, the position of the treatment instrument relative to the anatomy of the patient being permanently represented on the display unit during treatment. The monitoring and representing of the position of the treatment instruction takes place by way of the control software of the treatment device.

U.S. Pat. No. 5,230,623 proposes expanding the control software of a neurosurgical treatment device in such a way that the control signals permanently output by the treatment instrument can temporarily also be used to operate a menu represented on the display unit. In this way, different functions of the treatment device can be selected. Because the hardware and software prerequisites for detecting the position of the treatment instrument or for converting the spatial position into control signals are present anyway, only slight changes to the control software need to be made for this purpose.

SUMMARY OF THE INVENTION

In contrast to the foregoing, the object of the present invention is to expand a dental device in terms of hardware in such a way that conventional treatment instruments can additionally also be used as input devices for controlling the entire device.

The object of the present invention is thus to present a dental device in which the numerous functions of the equipment can be controlled in a way which is new, as user-friendly as possible, and effective.

The object is achieved by a device which has a treatment instrument, a central control device, a display unit and a detector which detects the spacial position of the treatment instrument, with the control device being arranged to convert the detected spacial position of the treatment instrument into coordinates for controlling a pointer in the display unit.

The device has at least one treatment instrument, a central control device and also a display unit, on which, for example, different operating parameters and functions of the device are represented. In accordance with the invention, the device furthermore has means for detecting the spatial position of the treatment instrument. In order to alter certain operating parameters represented on the display unit or in order to select a function, in a control mode, the spatial position of the treatment instrument is then converted into control signals for a pointer which is movable on the display unit. During the control mode, the treatment instrument thus takes over the function of an input device, with the method of functioning corresponding to that of a computer mouse, so that the entire dental device can be operated without contact and comfortably. In order to call up a certain function or to alter an operating parameter, it is therefore no longer necessary to put down the treatment instrument in order to actuate a special input instrument. As a result of this, the danger of contaminating an input instrument—for example a keyboard—which is often very difficult to clean or disinfect, is also avoided.

In this connection, by the treatment instrument referred to above is meant all of the instruments of a dental treatment area. In addition to the usual drill, this can be, for example, an intra-oral camera, a measuring head or suchlike. Fundamental in this connection is that a position-determining of these instruments on the basis of their method of functioning is not actually possible or necessary, but that in accordance with the invention, however, they can now additionally fulfil the function of an input instrument.

Developments of the invention are also disclosed herein. Thus, all known techniques can be used in order to establish the spatial position of the pointer instrument, for example the position-determining by means of ultrasonic pulses that is described in the laid-open publications EP 0 789 320 A2, EP 0 526 015 A1 and DE 38 38 605 A1. Preferably, however, the position is detected by emitting and receiving of infrared radiation. For example, an infrared light source can be provided on the display unit for this purpose. The radiation emitted by this light source is then reflected by a passive marker (reflector) mounted on the treatment instrument and detected by an optical sensor—for example a camera or a 4-field photodiode—which is in turn provided on the display unit. As an alternative to this, an active infrared light source can also be arranged directly on the treatment instrument, in which case the light sources on the display unit can then be dispensed with. The coordinates of the light source or of the reflector on the treatment instrument that are detected by the optical sensor are then converted into Cartesian coordinates on the display unit, as a result of which the position of the pointer can be altered by simple movement of the treatment instrument.

Because, in accordance with the invention, the treatment instrument is to take over the function of a mouse, it is advantageous if, in addition to the signals for moving the pointer, further control signals, which correspond, for example, to the pressing of a left-hand or right-hand mouse button, can be generated. The additional use of a foot switch, for example, can be provided for this purpose.

In a basic embodiment of the present invention, it is sufficient if only one active (infrared light source) or passive (reflector) marker is mounted on the treatment instrument. The possibilities for generating further control signals are, however, increased if there is at least one further marker on the treatment instrument, because the possibility is now given of detecting in addition to the position of the instrument the spatial orientation thereof as well. The spatial orientation or alterations thereof can then be taken into account when generating additional control signals. If three markers are mounted on the treatment instrument, the precise 3-dimensional position of the instrument can be detected and used for control purposes.

As an alternative to this, there is the possibility of generating with the markers on the treatment instrument a signal which can change over time, which signal is detected by the camera and interpreted as an additional control signal. This signal which can change over time can, for example, be formed by different on/off sequences of the light source or the reflection properties of the reflector. The triggering of such sequences can, for example, take place by way of a switch mounted on the instrument. Likewise, by way of a signal which can change over time, the signal-to-noise ratio of the system can be improved, because the influence of other infrared sources (for example reflections at a lamp or a button) is minimised in this way.

Advantageously, the use of a conventional mouse is still to be possible in parallel with the use of the treatment instrument as the input device.

According to another aspect of the invention, there is provided a novel method for controlling a dental device which has at least one treatment instrument, a central control device and a display unit. This novel method involves the detection of the spacial positioning of the treatment instrument and the conversion of this positioning into coordinates for controlling and operating a pointer on the display unit.

BRIEF DESCRIPTION OF THE DRAWINGS

In the following, the invention is to be explained in greater detail with the aid of the accompanying drawings, in which:

The general structure of a dental treatment area is already sufficiently known from the prior art. In FIG. 1, therefore, only the elements which are essential to the invention are shown. These are a treatment instrument 1—a drill in the example which is shown—and also a display unit (monitor) 2 and a central control device (not shown). On the screen of the monitor 2 can be displayed, for example, the operating data of the treatment instrument 1 in use in each case, maintenance notes, patient data in text and/or image, and various adjustable and permanently specified functions of the treatment area, as well as any computer programs. In order to allow a clear representation, different functions can be called up with the aid of a menu 7. In this connection, for a treatment to be carried out in a plurality of steps, there is also the possibility of selecting for each step operating parameters and functions which have already been programmed in beforehand. The selecting of certain functions and the altering of operating parameters takes place by selection of the appropriate symbols on the surface of the screen by the pointer 3.

Figure 1:
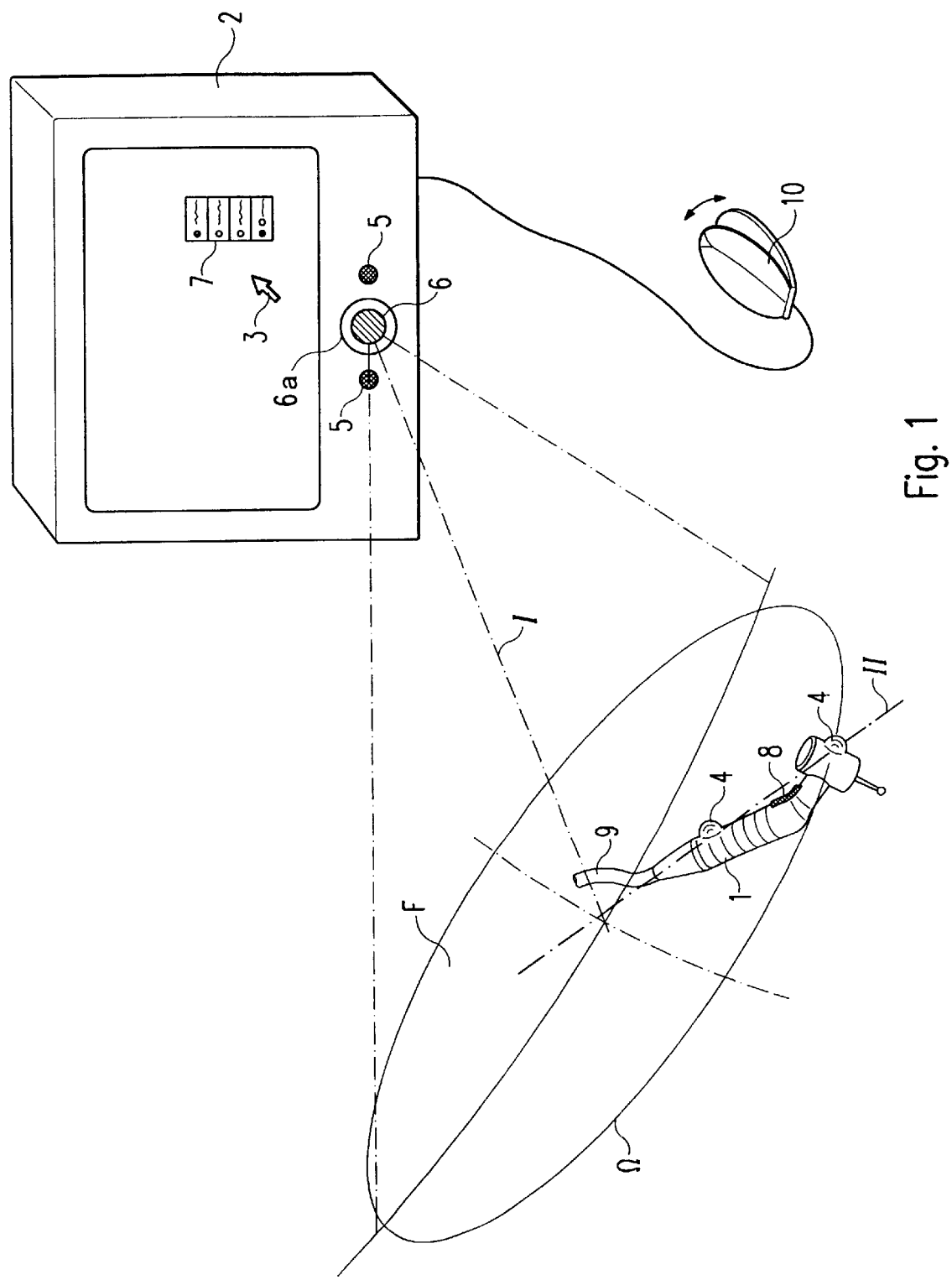
FIG. 1 shows an exemplary embodiment of a dental device in accordance with the invention.

In accordance with the invention, the pointer 3 is controlled in a control mode with the aid of the treatment instrument 1 which serves as an input device. For this purpose, two passive infrared markers (reflectors) 4 are mounted on the treatment instrument 2. On the lower side of the screen 2 are two infrared light sources 5—for example IR-LEDs—by way of which the instrument 1 is illuminated. The reflections of the infrared light by the two markers 4 arranged on the treatment instrument 1 are detected by an infrared-sensitive camera 6, which is likewise mounted on the lower side of the screen 2. The camera 6 is preferably provided with a daylight blocking filter 6a in order to increase the signal-to-noise ratio with respect to environmental influences. The solid angle $\Omega$ which can be detected by the camera 6 is identical to the area irradiated by the two light sources 5.

In the following, the method of functioning of the camera 6 is explained in greater detail. By the camera 6, the two markers 4 are detected and their spherical coordinates with respect to the optical axis I of the camera 6 are calculated. In this connection, the distance of the treatment instrument 1 from the camera 6 can be chosen arbitrarily within certain limits. The calculated spherical coordinates are then converted by the control unit to cartesian coordinates for the screen surface and the pointer 3 is represented in the corresponding position. In this way, during the control mode, the pointer 3 can be moved over the surface of the screen 2 by simple movement of the treatment instrument 1. In this connection, the sensitivity in the case of the conversion to cartesian coordinates is inversely proportional to the distance of the two markers 4 from the camera 6 and can thus be varied by the user in a deliberate way. In order to carry out fast and thus also coarse movements of the pointer 3, the treatment instrument 1 needs to be at only a small distance from the camera 6, while at a greater distance, slow but precise movements of the pointer 3 can be achieved.

The movement of the pointer 3 by the treatment instrument 1 can take place absolutely or relatively. In the first case, each position of the treatment instrument 1 in the solid angle Ω detected by the camera 6 corresponds exactly to a coordinate of the pointer 3 on the screen. In the second case, the position of the pointer 3 is altered by the movement of the treatment instrument 1 relative to the position of the pointer 3 at the start of the control mode. This case corresponds to the behaviour of a standard mouse. The intervening interruption of the pointer movement that takes place as a result of lifting in the case of the normal computer mouse can be simulated by an additional switch or by ignoring very fast movements.

As an alternative to the camera 6, a 4-field photodiode or a plurality of photodiodes arranged in a manner such that they are distributed could be used as the optical sensor. The detected signals are then converted into corresponding coordinates with the aid of a centre-of-gravity calculation.

In order to be able to select, for example, one of the functions of the menu 7 represented on the screen 2, the possibility must further exist of being able to generate additional control signals, which correspond to a mouse click, for example. For this purpose, an additional switch 8 can be provided on the treatment instrument 1. When this switch 8 is actuated, for example, corresponding control signals are passed via the connecting tubing 9 to the central control device. As an alternative to this, it could also be provided that when the switch 8 is actuated, a signal which can change over time is generated, which signal is detected by the camera 6 and interpreted as a corresponding mouse click. By way of example, as a result of changes to the reflection properties of the markers 4 with the aid of polarisation foils, an on/off sequence with respect to time can be generated.

Figure 2A:
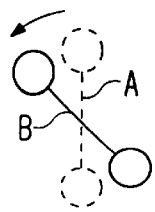
FIGS. 2a to 2c show diagrammatic representations for generating additional control signals when two markers are used.
Figure 2B:
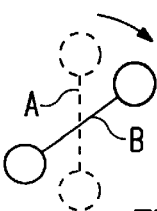

If the switch 8 has two switch states to be selected, then in a simple way a right-hand and a left-hand mouse click can be imitated. If, however, the switch 8 offers only the possibility of a single switch state, then first of all only one control signal can be generated. In this case, the orientation of the treatment instrument 1 can additionally be taken into account. In fact, in order to calculate a cartesian coordinate for the pointer 3, firstly only a single marker 4 is sufficient. But by the second marker, a straight line II is defined, the vertical position of which in space can be calculated by the central control unit. The alignment of the projection of these straight lines II in a plane F perpendicular to the optical axis I of the camera 6 can then be evaluated for additional control functions. By way of example, it is possible to distinguish between a right-hand or a left-hand mouse click on the basis of the alignment of the straight lines II. Preferably, however, instead of the absolute orientation of the treatment instrument 1, an alteration of the orientation is used to generate the additional control signals. By way of example, it can be provided that after actuation of the switch 8, a distinction is made as to whether the treatment instrument 1 is rotated in the clockwise direction or in the anti-clockwise direction, something which then corresponds to the right-hand or left-hand mouse click. This is represented in FIGS. 2a and 2b, with A denoting in each case the orientation of the instrument axis before the rotation and B its orientation after the rotation. Accordingly, the rotation in the anti-clockwise direction that is represented in FIG. 2a is associated with the click of a left-hand mouse button and the rotation represented in FIG. 2b is associated with a right-hand mouse click.

Because, however, there is the danger that the pointer is also displaced when the treatment instrument 1 is rotated, it can be provided that the pointer 3 is no longer moved while the switch 8 is actuated, and instead a distinction is made only between the different directions of rotation of the instrument 1. If the instrument 1 is provided with three markers 4, the absolute position of the instrument 1 (rotated to the left or right) can also be used and associated with a corresponding click of the left-hand or right-hand mouse button.

A further possibility consists in using a foot switch 10 connected to the central control unit and the monitor 2 in order to generate the additional control signals. In this case, the switch 8 on the treatment instrument 1 can be dispensed with. If the foot switch 10 has only one switch surface, then as already described, different control signals can be generated with the aid of rotations of the treatment instrument 1.

The foot switch 10 or the switch 8 on the treatment instrument 1 can also be used to activate the control mode. Alternatively, it is possible to establish that the control mode is activated as soon as signals of the markers 4 are detected by the camera 6 over the duration of a pre-defined and adjustable time window. If this control mode is activated, the foot switch 10 can be used to generate the additional control signals. After the control mode has ended, it again carries out its usual functions (starter, etc.), which are dependent on the instrument which is activated in each case.

Instead of the use of passive markers 4, active light sources can also be provided on the treatment instrument 1, in which case the infrared light sources 5 on the display unit 2 can then be dispensed with. The markers are then preferably integrated in the coupling between the detachable instrument and the supply tubing, because, on the one hand, an appropriate supply of current is then available and, on the other hand, the instruments themselves do not need to be redesigned. In the case of passive markers on the other hand, a separate holding device can also be used, for example in the form of a clamping ring or suchlike, which is slipped on to or pushed on to the treatment instrument.

Figure 2C:
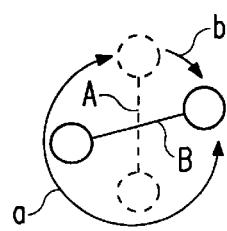

Furthermore, instead of one or two markers, three markers can also be mounted on the instrument 1, something which is advantageous if the precise 3-dimensional arrangement of the treatment instrument 1 is to be used to generate additional control signals. If there are three markers in a triangular arrangement (in which case this may not be an equilateral triangle), the absolute orientation of the instrument 1 in space can be determined. In contrast to this, when only two markers are used, ambiguities result, because it is not possible to distinguish between positions rotated by 180°. As represented by way of example in FIG. 2c, there is the danger that it is no longer possible to derive from the end position B whether a left-hand rotation a or right-hand rotation b took place.

When three markers or two spatially separated image sensors are used, there is furthermore the possibility of using the third dimension to operate the treatment unit. By way of example, different functions of the work station can be controlled automatically depending on the distance of the treatment instrument 1 from the display unit 2; if the treatment instrument 1 is close to the display unit 2, for example, the patient chair can be controlled, at a medium distance a control menu for a camera shot is automatically opened, and at a large distance a menu surface for power acquisition is represented. In this way, the change-over between different menu surfaces or the leafing through a program would be simplified.

In order to generate control signals corresponding to the mouse clicks, or even further control signals in addition to this, a speech recognition module can also be provided on the treatment unit.

Once the corresponding function has been carried out on the screen surface with the aid of the treatment instrument 1 functioning as the input instrument, the control mode can be deactivated and the treatment instrument 1 again used in its original function in the usual way. If the dental device contains a plurality of treatment instruments, each of these instruments can function as the input instrument during the control mode. If the instruments have passive markers, the markers of the instruments in the instrument tray are hidden anyway, so that they cannot lead to an interfering signal. If active markers are present in each case, sensors can be mounted in the instrument tray which allow the generation of infrared signals only in the case of markers of an instrument which has been taken out.

Thus, the entire dental device can be controlled without contact in a simple and effective way. Furthermore, no additional input devices which the dentist has to actuate with his possibly contaminated fingers are necessary, because the treatment instrument 1 can be held continuously in the hand. If passive markers are used, the treatment instruments 1 can also be cleaned and sterilised without great difficulties. Preferably, however, the dental device also has a conventional mouse, which can be used in parallel with the treatment instrument 1 as an input instrument.

In the following, with the aid of FIGS. 3a to 3c, the possibilities for generating additional control signals that result in the case of different marker arrangements will be explained briefly.

Figure 3A:
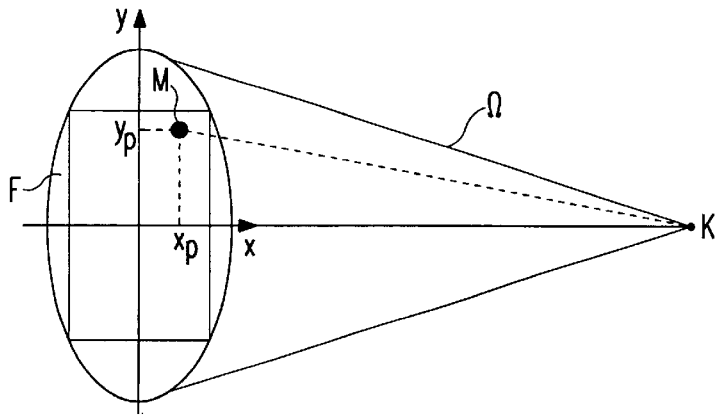
FIGS. 3a to 3c show diagrammatic representations of different marker arrangements.

FIG. 3a shows a sketch for the use of a single active or passive marker M on the treatment instrument. The detecting of this marker M allows the establishing of its position within the plane F placed in the cone of vision Ω of the camera K. The position of the marker M can then be converted into corresponding screen coordinates $x_p$ and $y_p$ for the pointer on the screen. Because there is only one marker M, additional control signals for simulating mouse clicks can be generated only by an additional input instrument—for example the foot switch—or by generating special light sequences.

Figure 3B:
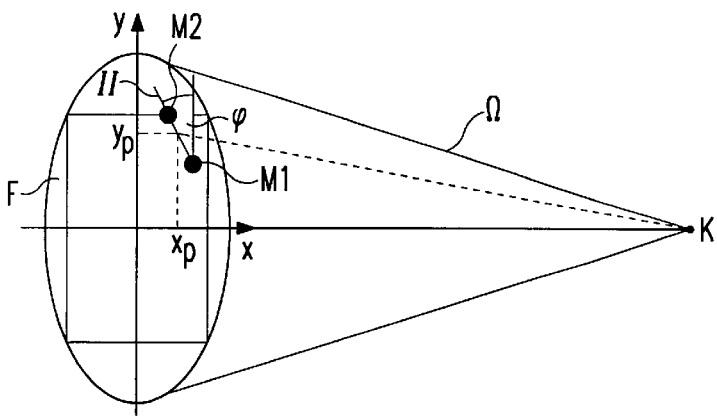
Figure 3C:
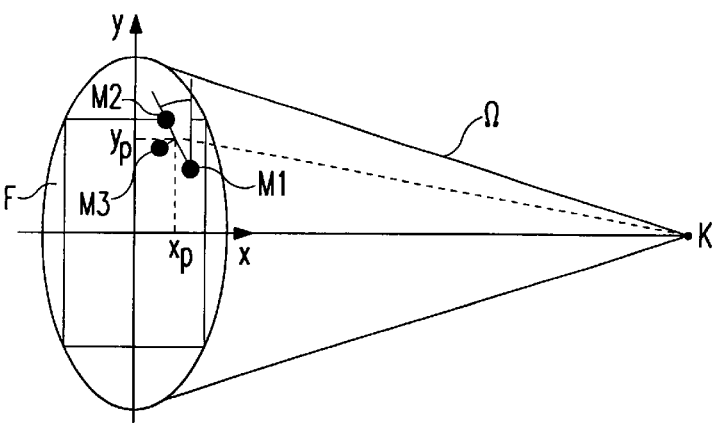

In the example shown in FIG. 3b with two markers M1 and M2, in addition to the position-determining of the two markers, the orientation of the connecting straight lines II relative to the x axis or y axis can also be established. The angle Φ determined in this connection can, as described above—possibly with the aid of a further switch or foot switch—be used to generate further control signals. The centre point between the two markers M1 and M2 is preferably chosen for the coordinates $x_p$ and $y_p$ of the pointer on the screen surface. However, if the two markers M1 and M2 are identical in construction, a reversal of their arrangement, which results, for example, in the case of a rotation about 180°, cannot be detected, so that ambiguities can possibly result. As already mentioned, this arrangement therefore has the disadvantage that the rotation of the instrument cannot be determined unambiguously, because in the case of a rotation out of any position about 180°, exactly the same mapping of the marker arrangement results. However, there is the possibility of getting round this problem by constructing or operating the markers in such a way that they can be identified unambiguously. This can, for example, take place by way of a different shape of the markers or by modulation of the light signals emitted by the markers.

The ambiguities described above in the case of the example shown in FIG. 2b can finally be ruled out by the use of three markers M1 to M3, because now the exact orientation and position of the instrument in space can be determined. Here also, there is the possibility of using different orientations to generate additional control functions. But because, as a rule, a foot switch is present anyway in a dental device, the use of a single marker or two markers is to be preferred.

What is claimed:

1. Dental device comprising: at least one treatment instrument, a central control device and a display unit, means for detecting the spatial position and the spatial orientation of the at least one treatment instrument, said central control device being constructed to convert, when in a control mode, the detected spatial position of the at least one treatment instrument into coordinates for controlling the position of a pointer on the display unit for selecting different functions represented on the display unit, and said central control device also being constructed to respond, when in said control mode, to the detected spatial orientation of said at least one treatment instrument to produce a function of a right mouse click and a function of a left mouse click according to whether the at least one treatment instrument is rotated in a clockwise direction or an anti-clockwise direction thereby to control selection of alternate functions according to the detected spatial orientation of the at least one treatment instrument.

2. Dental device according to claim 1, wherein the means for detecting the spatial position and the spatial orientation of the at least one instrument on the display unit have at least one infrared light source and an optical sensor, and at least one reflector mounted on the at least one treatment instrument for reflecting the radiation emitted by the at least one infrared light source.

3. Dental instrument according to claim 1, wherein the means for detecting the spatial positions of the treatment instrument have at least one infrared light source mounted on the treatment instrument, as well as an optical sensor arranged on the display unit.

4. Dental instrument according to claim 2, wherein the optical sensor is an infrared-sensitive camera.

5. Dental device according to claim 2, wherein the optical sensor is a 4-field photodiode.

6. Dental device according to claim 1, further including means for generating control signals for the pointer during the control mode.

7. Dental device according to claim 6, further including a switch device mounted on the at least one treatment instrument for generating the control signals.

8. Dental device according to claim 6, further including a foot switch for generating the control signals.

9. Dental device according to claim 1, further including a device for generating further control signals, comprising a speech recognition module.

10. Dental device according to claim 1, further including a switch for activating the control mode.

11. Method for controlling a dental device which has at least one treatment instrument, a central control device and a display unit, said method comprising the steps of detecting the spatial positions as well as the spacial orientations of the at least one treatment instrument, converting said spatial positions into coordinates for controlling and operating a pointer on the display unit to select different functions, and producing left mouse click signals and right mouse click signals according to whether the at least one treatment instrument is rotated in a clockwise direction or an anti-clockwise direction, for selecting alternate functions.

* * * * *